US00PP07902P

United States Patent [19]

Marciel

[11] Patent Number: Plant 7,902

[45] Date of Patent: Jul. 7, 1992

[54] ROSE PLANT NAMED DEVTINTA

[75] Inventor: Stanley G. Marciel, Aptos, Calif.

[73] Assignee: DeVor Nurseries, Inc., Watsonville, Calif.

[21] Appl. No.: 608,529

[22] Filed: Nov. 2, 1990

[51] Int. Cl.[5] ..... A01H 5/00

[52] U.S. Cl. ..... Plt./21

[58] Field of Search ..... Plt./20, 21

[56] References Cited

U.S. PATENT DOCUMENTS

PP. 6,264 8/1988 Olesen et al. ..... Plt. 20

PP. 6,910 7/1989 Carruth et al. ..... Plt. 21

*Primary Examiner*—Howard J. Locker

*Attorney, Agent, or Firm*—Charles W. Rummler

[57] ABSTRACT

A new and distinct greenhouse rose plant particularly distinguished by its continuous and abundant production of large flowers having a generally currant red coloration from early Spring to Winter. The long lasting flowers are borne singly on sturdy stems of medium length from a vigorous, upright plant of about 200 cm. in height, having abundant glossy foliage.

1 Drawing Sheet

BACKGROUND OF THE NEW PLANT

This new rose plant originated as a seedling growing among a collection of rose plants maintained in my nursery at Pleasanton, Calif. for breeding purposes. Because of the large size of the blooms of this plant, their very pleasing coloration, and the glossy foliage, I decided that this plant was an ideal subject for propagation and test for commercial purposes and propagation was done under my direction by budding at my nursery in Wasco, Calif. This was done through several generations at Wasco which demonstrated satisfactorily that the novel characteristics of this new plant would hold true from generation to generation and appeared to be firmly fixed.

This plant is now being reproduced on a commercial scale in nurseries at Orland, Wasco, and Watsonville, Calif.

DESCRIPTION OF THE DRAWING

My new rose plant is illustrated by the accompanying full color photographic drawing which shows a face view of a fully opened flower, the colors shown being as nearly true to those herein specified as is reasonably possible to obtain by conventional photographic procedures.

DESCRIPTION OF THE NEW VARIETY

The following is a detailed description of my new rose plant based upon observation of plants grown in greenhouse at Orland, Calif., with the color designations specified herein being according to The R.H.S. Colour Chart published by The Royal Horticultural Society of London, England.

THE PLANT

Origin: Seedling.

Parentage:

*Seed parent.*—Plant No. 79218-2 (unpatented).

*Pollen parent.*—Plant No. 79051-5 (unpatented).

Classification:

*Botanic.*—Hybrid tea.

*Commercial.*—Greenhouse rose.

Form: A tall, upright rose bush.

Height: Aproximately 200 cm. high.

Growth habit: Vigorous, upright and very sturdy.

Main stem:

*Length.*—About 50 cm. — 80 cm. from the last flower cut or a point above a 5 part leaf which will encourage initiation of a new shoot eminating from the bud eye at the base of the leaf which would grow to produce a flower producing stem.

*Color.*—Yellow green, 146-A.

*Branching character.*—Free branching.

Foliage:

*Quantity.*—Abundant.

*Number of leaves.*—About 5 from the last flower cut.

*Size.*—About 150 mm. long.

Leaflets:

*Number.*—3 or 5.

*Shape.*—Ovate with denticulate margin.

*Size.*—Terminal leaflet about 85 mm. long.

*Texture.*—Leathery.

*Aspect.*—Smooth and glossy.

*Color of leaflets.*—Upper side — Yellow green 147-A Under side — Yellow green 147-B.

Stipules: Adnate.

Rachis: About 160 mm. on leaf having 5 leaflets; about 125 mm. on leaf having 3 leaflet.

*Petioles.*—About 10 mm. on 3 leaflets and about 20 mm. on 5 leaflets.

Ribs and veins: Slightly grooved on top and bottom.

Thorns:

*Size.*—Varying in size, about 10 to 15 mm. long.

*Color.*—Greyed orange 176C tipped with yellow-green 152-D.

THE BUD

Size: Medium.

*Diameter.*—About 25 mm.

*Length.*—About 45 mm.

Shape: High-centered and pointed.

Rate of opening: Slow.

Color of petals:

*When sepals first divide.*—Red 53-A.

*when petals begin to unfurl.*—Red 46-A.

Sepals:

*Number.*—Five.
*Shape.*—Spreading with small leafs protruding.
*Character.*—The sepals curl back when flowers open.
*Color.*—Inside — Yellow-Green 146-B. Outside — Yellow-Green 144-A.

Calyx:
*Shape.*—Funnel shaped.
*Width.*—About 13 mm.
*Length.*—About 10 mm.
*Size.*—Large.
*Splitting.*—Calyx does not split.
*Aspect.*—Smooth.

Flower stem:
*Length.*—About 90–105 mm.
*Character.*—Erect, rigid and sturdy.
*Color.*—Yellow-Green 146B.

THE FLOWER

Blooming habit: Continuous and abundant from early Spring through mid-season and Fall, blooming freely under greenhouse conditions.

Size of bloom: Large.
*Diameter.*—About 90 mm.
*Depth.*—About 35 mm.

Borne: Singly on strong, upright stems.

Shape:
*When bloom first opens.*—High center.
*When bloom matures.*—The petals become nicely imbricated.

Petalage:
*Number.*—About 28.

Arrangement: Imbricated.

Form: Spoon-shaped with slightly lobed margins.

Texture: Leathery, but soft.

Appearance: Velvety.

Color:
*Outer petals.*—Currant Red 46-A with base of Yellow 8-D.
*Reverse side.*—Red 53-B with base of 4-D.
*Inside petals.*—Currant Red 46-A with base of Yellow-white 158-D.
*Reverse side.*—Red 53-B with base of Yellow-white 158-C.

Petaloids:
*Number.*—About 5 to 9.

*Size.*—About 20 mm. long.
*Color.*—Red 53A with a base of Yellow 2-C.

Flower stem:
*Length.*—About 90 to 105 mm.
*Color.*—Yellow Green 146-B.
*Character.*—Sturdy and upright.

Fragrance: Very slightly fragrant.

Persistence: In greenhouse environment, flower hangs on and dries.

Discoloration after full bloom: Flower does not discolor.

Disease resistance: Resistant to mildew, rust, and black spot as observed at Watsonville, Calif.

Lasting quality: On the plant, and as a cut flower, very long lasting.

THE REPRODUCTIVE ORGANS

Stamens:
*Number.*—About 116–145.
*Arrangement.*—Introrse.
*Anthers.*—Size: About 3 mm. Color: Yellow Orange 22-B.

Filaments:
*Length.*—About 5 to 10 mm.
*Color.*—Red Purple 60-A.

Pollen:
*Color.*—Yellow Orange 22-B.

Pistils:
*Number.*—About 92 to 105.
*Styles.*—Length: About 10 mm. Color: Red 53-D at top changing to green 145-D along the stem.

Stigmas:
*Color.*—Greyed Red 179-C.

Character of the ovaries: Small, oval-shaped and covered all over with silvery threads.

Fruit: Fertile.
*Shape.*—Pear-shaped.
*Color.*—Green-Orange 166-C.

I claim:

1. A new and distinct variety of rose plant, substantially as herein shown and described, characterized by its abundant and continuous production of large currant red flowers, which have a long lasting vase life; by its vigorous upright growth habit with glossy foliage and its sturdy upright stems.

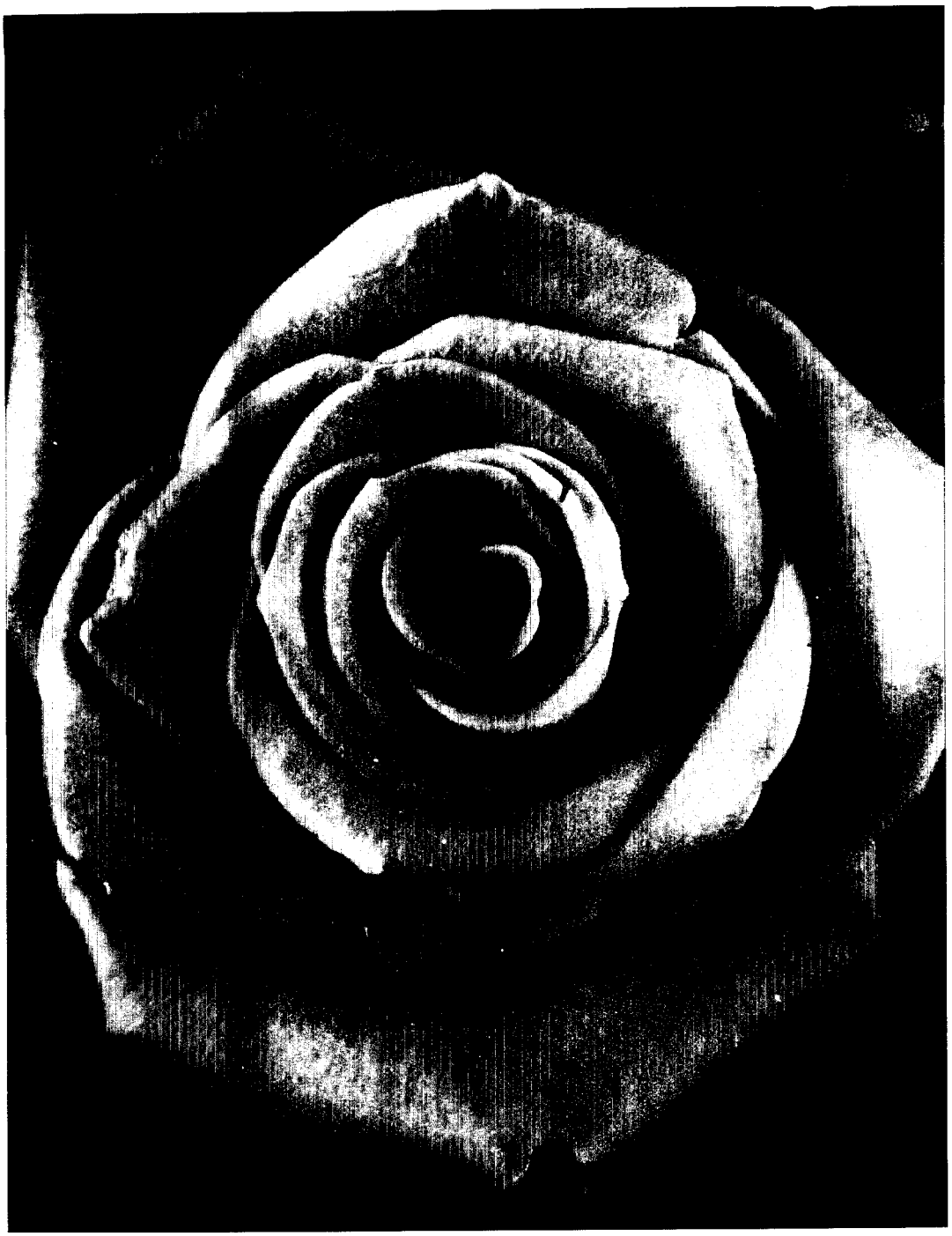

* * * * *